(12) United States Patent
Livingston

(10) Patent No.: US 6,266,996 B1
(45) Date of Patent: Jul. 31, 2001

(54) SIMPLE AND INEXPENSIVE METHOD AND DEVICE FOR MEASURING CONCENTRATION AND RATE OF CHANGE OF A CRYSTAL ETCHANT GAS, SUCH AS HF OR DF GAS

(75) Inventor: Peter M. Livingston, Palos Verdes Estates, CA (US)

(73) Assignee: TRW Inc., Redondo Beach, CA (US)

( * ) Notice: Subject to any disclaimer, the term of this patent is extended or adjusted under 35 U.S.C. 154(b) by 0 days.

(21) Appl. No.: 09/167,197

(22) Filed: Oct. 6, 1998

(51) Int. Cl.[7] .................. G01N 17/02; G01N 9/00
(52) U.S. Cl. .......... 73/24.01; 73/24.06; 73/64.46; 73/579; 73/590
(58) Field of Search .............. 73/24.01, 24.06, 73/31.03, 64.44, 64.46, 64.41, 579, 590

(56) References Cited

U.S. PATENT DOCUMENTS

| | | | |
|---|---|---|---|
| 3,879,992 | * | 4/1975 | Bartera .................................... 73/30 |
| 4,674,319 | * | 6/1987 | Muller et al. ............................ 73/23 |
| 4,783,987 | * | 11/1988 | Hager et al. ........................ 73/32 A |
| 5,028,394 | * | 7/1991 | Lowell, Jr. et al. ................... 422/58 |
| 5,117,146 | * | 5/1992 | Martin et al. .................... 310/313 R |
| 5,208,162 | * | 5/1993 | Osborne et al. ......................... 436/6 |
| 5,795,993 | * | 8/1998 | Pfeifer et al. ...................... 73/24.01 |
| 5,877,407 | * | 3/1999 | Cadet et al. ........................ 73/24.01 |
| 5,958,787 | * | 9/1999 | Schonfeld et al. .................... 436/116 |

OTHER PUBLICATIONS

AARL Handbook for Radio Amateurs, 1998 edition, Published by the American Radio Relay League, pp. 14.26, 15.13.

* cited by examiner

*Primary Examiner*—Hezron Williams
*Assistant Examiner*—David J. Wiggins
(74) *Attorney, Agent, or Firm*—Michael S. Yatsko

(57) ABSTRACT

A method and device for determining concentration and rate of change of concentration of a gas having ability to act as crystal etchant, such as hydrofluoric acid (HF) or deuterium fluoric acid (DF) gas. A crystal 22 is placed in a chamber and subjected to erosion by the gas. The crystal resonant frequency, changeable during the crystal erosion, is determined and a crystal resonant frequency change is calculated to determine the concentration of the gas. The crystal 22 is preferably an AT-cut quartz crystal. The step of obtaining the crystal resonant frequency is preferably performed in a Colpitts oscillator. The step of calculating the gas concentration, proportional to the change in the crystal resonant frequency, may also encompass calculating a change and rate of change in the gas concentration, and averaging the calculated gas concentration. The crystal 22 is preferably inserted in a crystal holder 20, and mounted on an electronic box 34 which holds the oscillator board. The crystal 22 is partially protected with a cover 30 and is easily replaceable.

33 Claims, 4 Drawing Sheets

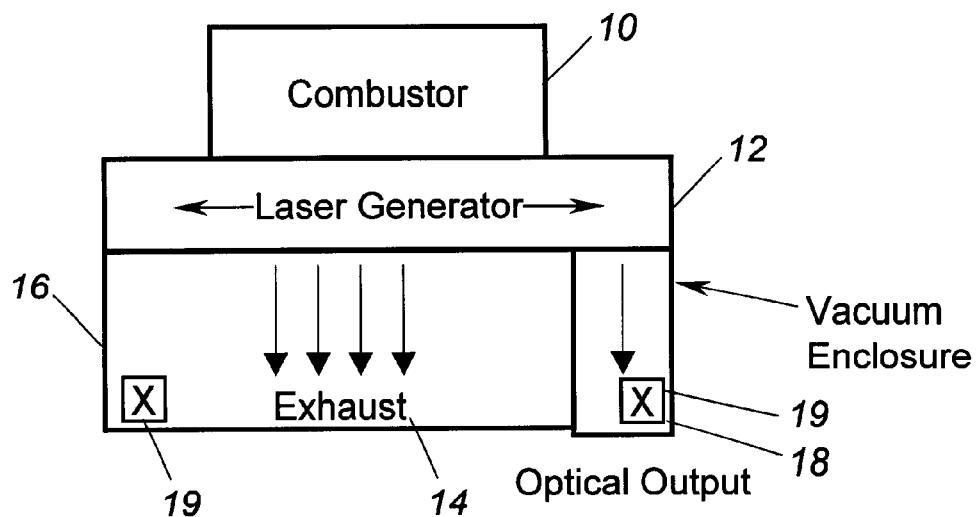
Figure 1
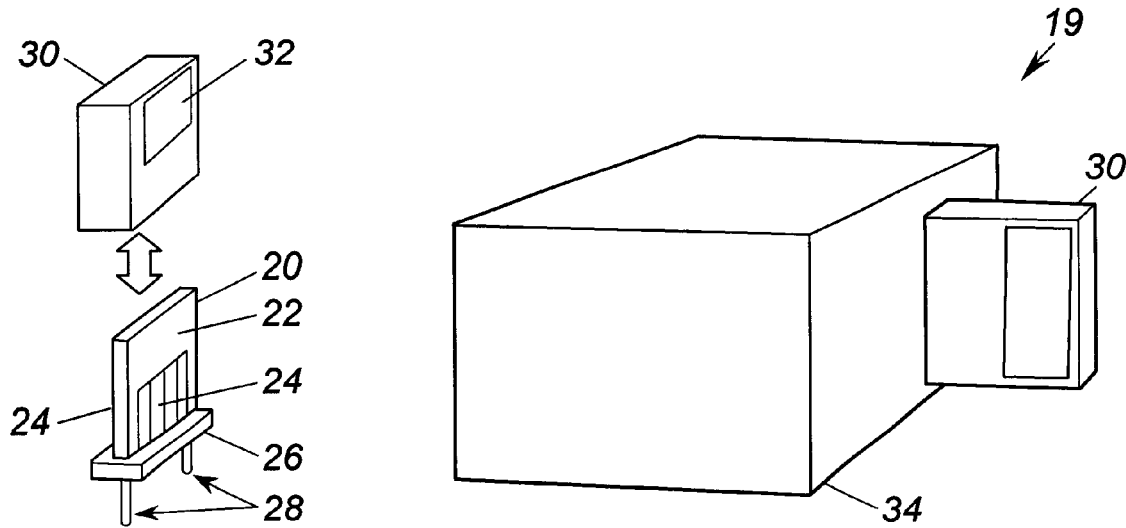
Figure 2  Figure 3

SIMPLE AND INEXPENSIVE METHOD AND DEVICE FOR MEASURING CONCENTRATION AND RATE OF CHANGE OF A CRYSTAL ETCHANT GAS, SUCH AS HF OR DF GAS

BACKGROUND OF THE INVENTION

1. Field of the Invention

The present invention relates generally to the field of gas sensors, and more particularly to a method and device for measuring concentration and rate of change of concentration of a gas having ability to act as crystal etchant, such as hydrofluoric acid (HF) or deuterium fluoric acid (DF) gas.

2. Description of the Related Prior Art

Chemical lasers, employable in electronic warfare systems, use hydrofluoric acid (HF) or deuterium fluoric acid (DF) gas. To properly diagnose laser operation and to prevent damage to optical elements, it is desirable to be able to determine the concentration and rate of change of the HF or DF gas at several locations in the laser resonator beam path. Therefore, the device should be small and inexpensive so that multiple units may be placed in the same chamber or laser resonator beam path. Presently, there are no such devices available.

The appropriate measuring device should behave as a dosimeter and be able to measure the presence and rate of change of ground-state HF or DF gas in the laser resonator beam path. The HF or DF sensor should further be able to discriminate against other chemical species present in the same chamber. Moreover, since the laser resonator beam path is a very inaccessible and hostile environment, the device should be sturdy and inexpensive, to justify replacement cost. Further, the device should be applicable to other industries which use HF or DF gas, such as semiconductor and oil-refining industries.

Therefore, there is a need for a simple, inexpensive, easily calibratible, efficient and highly sensitive HF or DF sensor, which can be manufactured at high operating margins, does not require a specialized, complicated fabrication process, and which can be used in different industries for measuring HF or DF concentration and rate of change.

SUMMARY OF THE INVENTION

The present invention consists of a method and a device for measuring concentration and rate of change of concentration of HF or DF gas in a chamber, such as a laser resonant beam path. Since the invention is based on subjecting a crystal to erosion by the measured gas, the device is also applicable to any other gaseous industrial crystal etchant.

One embodiment of the present invention is a method for determining concentration of a crystal etchant gas, such as hydrofluoric acid (HF) or deuterium fluoric acid (DF) gas, by subjecting a crystal to erosion by the gas, determining the crystal resonant frequency, which is changeable during the crystal erosion, and calculating the crystal resonant frequency change to determine the concentration of the gas. The step of obtaining the crystal resonant frequency is preferably performed in a Colpitts oscillator. The step of calculating the gas concentration, proportional to a shift in the crystal resonant frequency, may also encompass calculating a change in the gas concentration, calculating a rate of change in the gas concentration, and averaging the calculated gas concentration.

Another embodiment of the present invention is a device for determining concentration and rate of change of concentration of the gas. The device has a crystal being subjected to erosion by the gas, an element for determining the crystal resonant frequency, preferably an oscillator, and a calculating unit for determining the crystal resonant frequency change. The crystal is preferably an AT-cut quartz crystal. The crystal is inserted in a crystal holder, and mounted on an electronic box with the oscillator. It is partially protected with a cover, and can be easily replaced.

The foregoing and additional features and advantages of the present invention will become further apparent from the following detailed description and accompanying drawing figures that follow. In the figures and written description, numerals indicate the various features of the invention, like numerals referring to like features, throughout for the drawing figures and the written description.

BRIEF DESCRIPTION OF THE DRAWINGS

FIG. 1 is a simplified schematic illustration of a chemical laser showing possible locations for placement of a gas sensor of the present invention.

FIG. 2 is a schematic illustration of a crystal, crystal housing and cover of an exemplary implementation of the gas sensor, according to the preferred embodiment of the present invention.

FIG. 3 is a schematic illustration of the crystal housing cover of FIG. 2 and an electronic box of the gas sensor, according to the preferred embodiment of the present invention.

DETAILED DESCRIPTION OF THE INVENTION

Figure 4:
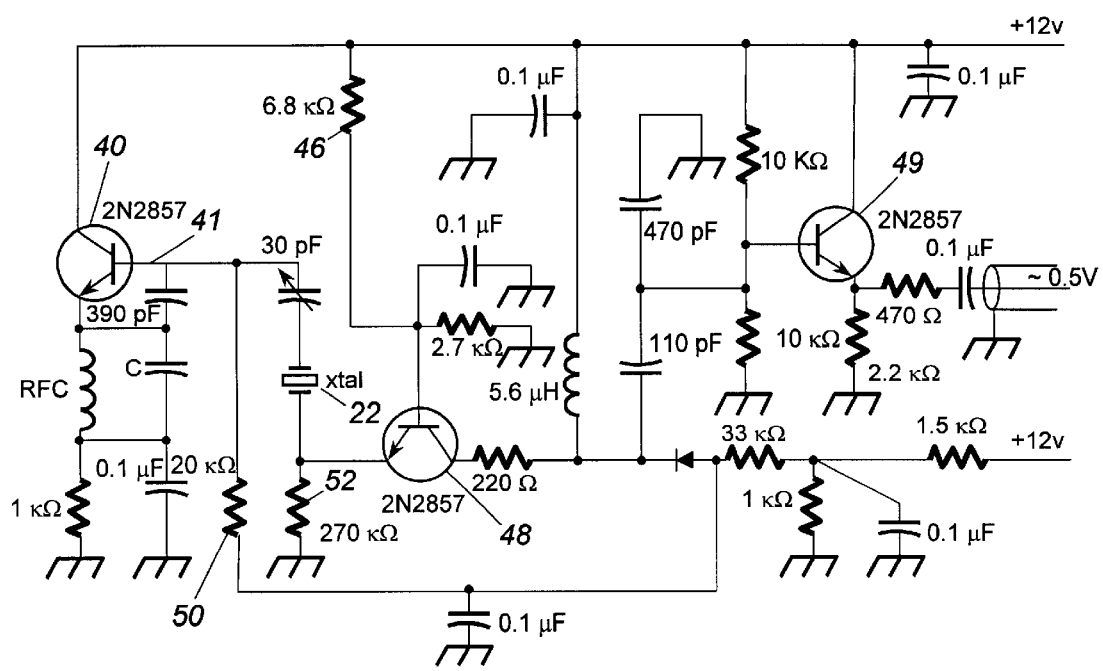
FIG. 4 is a schematic illustration of a conventional Colpitts oscillator, used in the preferred embodiment of the present invention.

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein with specificity.

One embodiment of the present invention is a method for determining concentration and rate of change of concentration of hydrofluoric acid (HF), by subjecting a crystal to erosion by HF gas, determining the crystal resonant frequency, which is changeable during the crystal erosion, and calculating the crystal resonant frequency change to determine the concentration of HF gas. The method is based on the fact that HF gas etches quartz crystal according to the reaction:

$$4HF + SiO_2 \rightarrow SiF_4\uparrow + 2H_2O\uparrow \tag{1}$$

As the reaction (1) goes to completion, the quartz crystal disappears as a gas and quartz crystal's mass is reduced. The same principle can be applied to deuterium fluoric acid (DF) gas and other gaseous crystal etchants. Throughout this document HF gas is chosen for convenience only, and it is presumed that the principles of the present invention equally apply to DF gas and other gaseous crystal etchants as well.

Quartz crystals are typically used to obtain radio-frequency (RF) waves with stable frequency. They are traditionally used in power sources of conventional radio transmitters. The crystal maintains a fixed frequency RF output at its resonance. The resonant frequency of crystal RF output is proportional to crystal mass. Thus, by removing some crystal mass, the resonant frequency of crystal RF output changes and becomes higher.

The step of obtaining the crystal resonant frequency is preferably performed in a Colpitts oscillator. The step of calculating the HF or DF concentration, proportional to a shift in the crystal resonant frequency, may also encompass calculating a change in the HF or DF concentration, calculating a rate of change in the HF or DF concentration, and averaging the calculated HF or DF concentration. The HF sensor of the present invention is relatively insensitive to the presence of fluorine F, either in atomic or molecular form, when there is no water present in the environment to form in-situ HF gas. However, if there is water vapor in the environment, the HF sensor of the present invention is capable of measuring crystal erosion related to the fluorine concentration as well, although HF or DF gas is the principal substance detected.

The other embodiment of the present invention is an HF sensor with a quartz crystal. The crystal is preferably AT-cut and block-shaped. When the device is placed in a container with the gas to be measured, the HF gas etches the quartz crystal according to the reaction (1), and increases the resonant frequency of crystal RF output. The frequency change can be measured in order to obtain the amount of crystal mass removed by the HF gas. Since the rate of crystal mass change is proportional to the concentration of HF molecules (or moles) per cubic centimeter of HF gas, the rate of frequency change is also proportional to the concentration of HF molecules. Therefore, the concentration of HF molecules can be obtained by measuring the frequency change of the crystal.

The change in resonant frequency $v_0$ of a crystal depends on concentration of HF gas $n_{HF}$ and can be represented with equation (2):

$$\frac{dv}{dt} = K n_{HF} \quad (2)$$

This formula assumes that all 4 HF molecules reacting the crystal according to reaction (1) do not need to strike a given $SiO_2$ molecule simultaneously, but form a surface complex with $SiO_2$ crystal until the $SiF_4$ reaction goes to completion. Therefore, the concentration of HF gas $n_{HF}$ is shown to the first power. Constant K should be determined experimentally, according to the application, although it is possible to derive its value from the first principles rules.

It is thus necessary to provide an equation for calculation of concentration of HF or DF gas, based on rate of change of crystal mass, which is dependent on the known rate of change in crystal frequency. According to a solution of the continuous medium problem for a rod geometry, provided by H. Goldstein, Classical Mechanics, Addison-Wesley Publishing Co., Inc., Cambridge 42, Mass., (1953), p. 355., which is pretty accurate when applied to a block-shaped crystal of the present invention, crystal's resonant frequency v can be calculated according to the following equation:

$$v = \frac{n}{2th} \cdot \sqrt{\frac{Y}{\rho}} \quad (3)$$

where n is the overtone number which is a constant, the square root of Young's modulus Y divided by the crystal density $\rho$ is the speed of sound in the crystal which is a constant, and th is the thickness of the crystal which changes with time. In order to determine the rate of change of crystal mass based on the rate of change in the crystal frequency, equation (3) is differentiated according to the equation:

$$\frac{\dot{v}}{v} = -\frac{\dot{th}}{th} \quad (4)$$

At location with total pressure of 5 torr and at 400° K, it can be determined that there are $1.2 \times 10^{17}$ HF gas molecules/$cm^3$. To determine the crystal erosion rate (rate of change of crystal mass) arising from the interaction of the quartz crystal with the gaseous hydrogen fluoride, reaction collision speed S, which is the number of HF molecules bombarding the crystal surface in a second, is determined according to the following equation:

$$S = \frac{1}{3} n_{HF} V A \quad (5)$$

where A is the crystal area exposed to the HF gas, V is the RMS gas molecule speed, and $n_{HF}$ is the concentration of HF. In this equation the factor ⅓ accounts for bombardment of two out of six faces of the crystal (front and back face facing the stream of HF gas), because, on the average, only ⅙ of all HF gas molecules move in any one direction.

The total mass of the crystal is determined according to the equation:

$$m = \rho A_t th \quad (6)$$

where $A_t$ is the surface area of the crystal, th is the thickness of the crystal, and $\rho$ is the density of the crystal.

Since four HF gas molecules are used to make one molecule of $SiO_2$ disappear, according to reaction (1), the mass-loss rate of quartz crystal molecules $MW_{SiO2}$ equals the ¼ of the product of the reaction collision speed S and the molecular weight of $SiO_2$ molecules $MW_{SiO2}$. The molecular weight of quartz $MW_{SiO2}$ is 60.02, its density $\rho$ is 2.65 grams/$cm^3$ and $N_A$ is Avogadro's constant. Moreover, the HF RMS molecular speed at temperatures of interest (about 450° K) is $V = 7.06 \times 10^4$ cm/sec. Therefore, the mass-loss rate of quartz crystal molecule is determined according to the equation:

$$\Delta m_{SiO_2} = \frac{1}{4} \cdot \frac{1}{3} \cdot MW_{SiO_2} n_{HF} V \cdot A, \quad (7)$$

According to equation (6) the rate of change of thickness th is determined as:

$$\delta th = \frac{\Delta m_{SiO_2}}{\rho A_t}. \quad (8)$$

Combining equations (4) and (8) the crystal frequency change can be determined according to the equation:

$$\Delta v = v_0 \frac{1}{4 \cdot 3} n_{HF} \frac{V \cdot A \cdot MW_{SiO_2}}{N_A \rho A_t} = 2.213 \cdot 10^{-19} \cdot n_{HF} v_0 \frac{A}{A_t} \quad (9)$$

Therefore, the concentration of HF gas $n_{HF}$ can be calculated from equation (9), when the crystal frequency change is known, because the sensitivity of the HF sensor is directly proportional to the chosen resonant frequency $v_0$.

In order to measure the change in crystal resonant frequency, the device of the present invention uses a conventional FM receiver technology, with crystal resonant frequency of 10.7 MHz, which makes the HF sensor of the present invention very sensitive. Because the HF sensor sensitivity is directly proportional to the chosen resonant frequency $v_0$ of equation (9), if the ratio of exposed area A to area of the crystal $A_t$ is ½, a 10 Hz/sec change in resonant frequency $v_0$, determined with the conventional FM receiver technology, is sufficient for detecting very small concentration of HF gas. The sensitivity threshold for detecting concentration of HF gas, calculated from equation (9), is the concentration of about $8.4 \times 10^{12}$ HF molecules/cm$^3$ of HF gas at partial pressure of 0.35 millitorr, which is much lower than $1.2 \times 10^{17}$ HF gas molecules/cm$^3$ mentioned above, at location with total pressure of 5 torr and at 400° K. If, however, higher crystal frequencies are needed, those skilled in the art can easily design a custom-made circuitry according to the principles of the present invention and well known crystal oscillator technology.

FIG. 1 is a simplified schematic representation of a chemical laser with two gas sensors of the present invention. The chemical laser consists of a combustor 10, a laser generator 12, an exhaust manifold 14, an enclosed optical laser resonator beam path 16, and an optical output 18. Chemical laser operation is described in a number of textbooks. See, for example, R. W. F. Gross, J. F. Bott, "Handbook of Chemical Lasers", John Wiley and Sons, New York, 1976. FIG. 1 illustrates two possible locations for a gas sensor 19 of the present invention, denoted with "X", and placed within the enclosed optical laser resonator beam path 16.

FIG. 2 is a schematic illustration of a crystal, crystal housing and cover of an exemplary implementation of the gas sensor 19, according to the preferred embodiment of the present invention. FIG. 2 illustrates a crystal holder 20 with a crystal 22 and plated electrodes 24, a mounting base 26 with mounting elements 28, and a slip-over protective cover 30 with windows 32. The slip-over protective cover 30 is placed over crystal holder 20 for protection. Mounting elements 28 allow easy replacement of the crystal 22. Mounting elements 28 are preferably plug-in pins, but could be any other type of mounting device able to facilitate attachment of the crystal holder 20 to an electronic box 34, presented in FIG. 3. The electronic box 34 encloses digital circuits illustrated in FIGS. 4 and 5, and supports the crystal holder 20. The electronic box 34 and the electrodes 24 must be well protected against gas corrosion. Crystal holder 20 has to be exposed to the gas in the enclosed optical laser resonator beam path 16, and thus protrudes from the electronic box 34, as shown in FIG. 3. Based upon the size of the components, presently crystal holder 20 has an area of 1×1 cm$^2$, and electronic box 34 has an area of 5×5 cm$^2$. They can probably be made even smaller.

Figure 5:
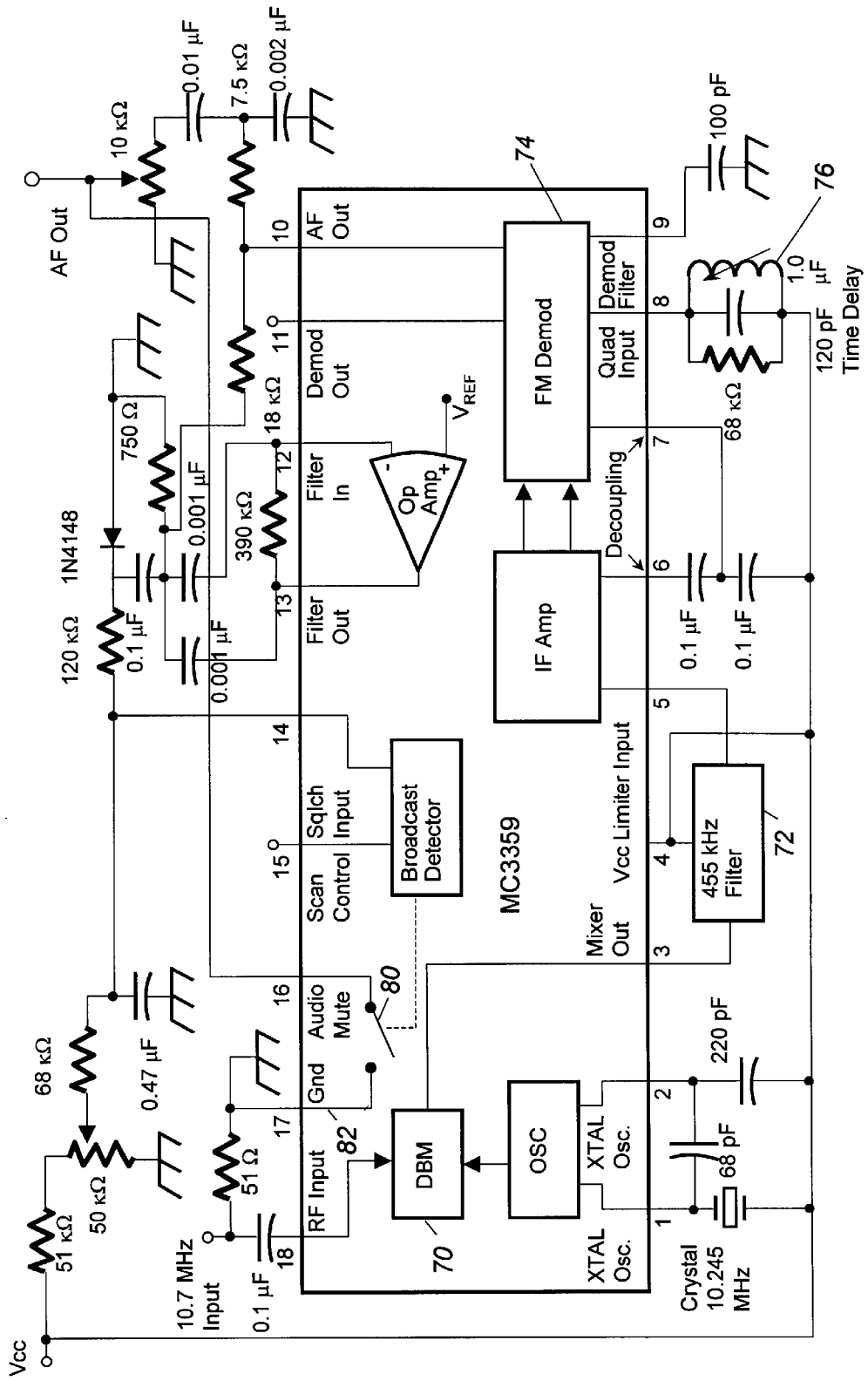
FIG. 5 is a schematic illustration of a conventional FM demodulator integrated circuit, used in the preferred embodiment of the present invention.
Figure 6:
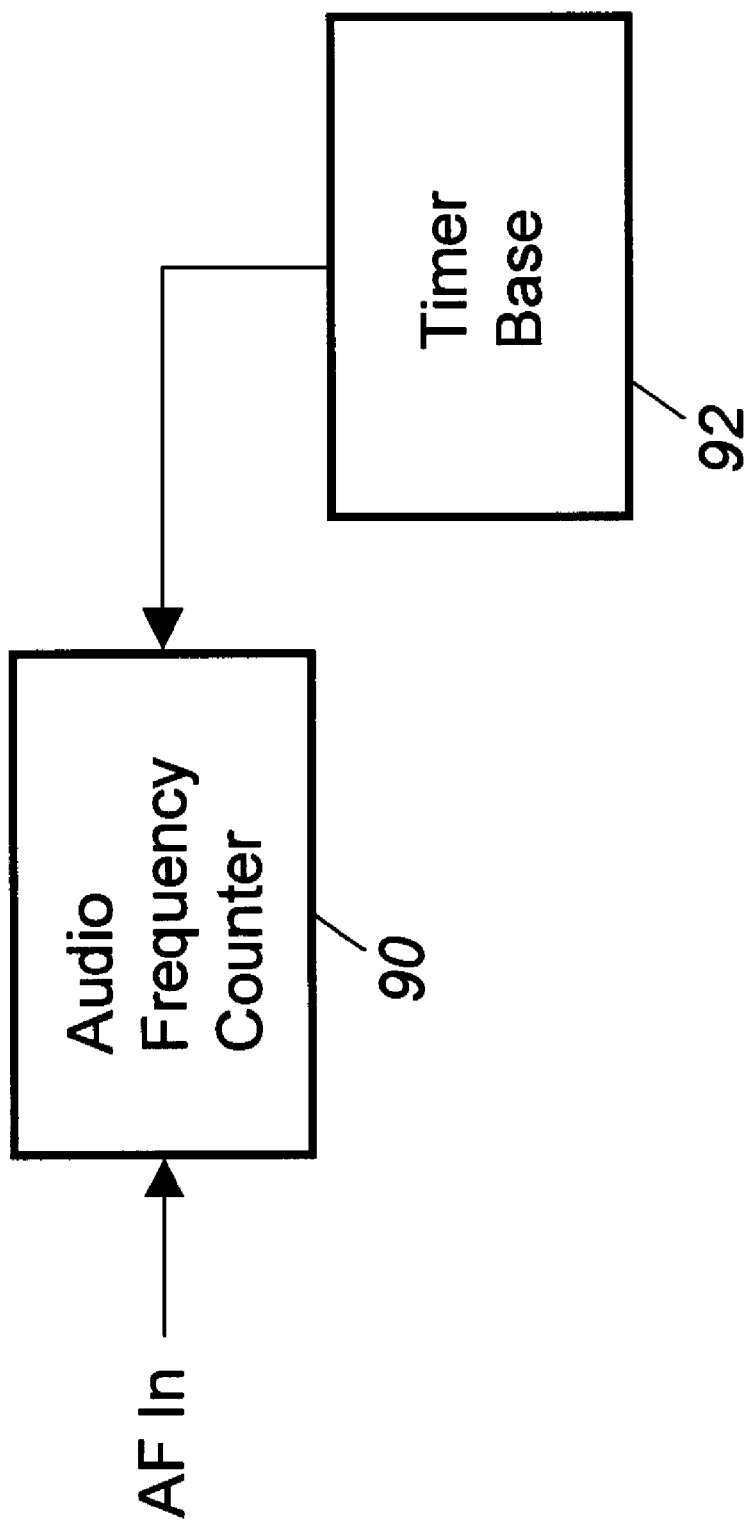
FIG. 6 is a schematic illustration of an audio frequency counter with a timer, according to the preferred embodiment of the present invention.

The digital circuits of the gas sensor 19 of the present invention consist of three parts: a Colpitts oscillator of FIG. 4, with automatic level control and an output amplifier driving a 50 ohm load, a conventional FM demodulator integrated circuit of FIG. 5, conventionally used in FM pocket radios, and an audio frequency counter with a timer of FIG. 6. FIGS. 4 and 5 and description thereof can be found in "ARRL Handbook for Radio Amateurs", 1998 edition, published by the American Radio Relay League, pages 14.26, 15.13, FIGS. 14.24 and 15.17.

If desired, the Colpitts oscillator of FIG. 4 and FM demodulator integrated circuit (IC) of FIG. 5 may be placed in the electronic box 34 upon which the crystal holder 20 is mounted, provided adequate shielding between the IC and the Colpitts oscillator is installed. Moreover, the electronic box 34 could be made as an autonomous device, independent of the laser or other type of gas chamber, if provided with its own, preferably 12 V, battery supply. Alternatively, the Colpitts oscillator and the crystal 22 may be mounted together and placed in the gas path, such as the laser resonator beam path 16. They may be coupled to the FM demodulator integrated circuit, placed outside the laser resonator beam path 16, by a coaxial cable, not shown. The coaxial cable is preferably a 50 ohm cable having leads for 12 volts dc outside power supply, and attached to a simple conventional decoupling network, not shown.

FIG. 4 is a schematic illustration of a conventional Colpitts oscillator, used in the preferred embodiment of the present invention, although other devices for determining the crystal resonant frequency could be used as well. A transistor 40 forms a Colpitts oscillator with the crystal 22, described in reference to FIG. 2, behaving as a bandpass filter (frequency trimmer) for the oscillator output. The base 42 of the transistor 40 is biased by a voltage divider 44, located from a 6.8 KΩ resistor 46, through an automatic level control (ALC) loop with a common-base transistor amplifier 48, and through a 20 KΩ resistor 50 at the oscillator base 41. The magnitude level of the output signal is sensed as a voltage drop over a 270 KΩ resistor 52, following the crystal 22. To prevent overload of the Colpitts oscillator, the common-base amplifier 48 is used to transform the Colpitts oscillator 10.7 MHz output signal from a high impedance output into a 0.5V signal driving a 50Ω load, and emitter follower 49 is used to buffer output from the load.

FIG. 5 is a schematic illustration of a conventional FM demodulator integrated circuit, used in the preferred embodiment of the present invention. Any other crystal resonant frequency detector for obtaining the crystal resonant frequency from the oscillator of FIG. 4, and supplying the crystal resonant frequency to the calculating device of FIG. 6 could be used as well. This circuit is a part of a conventional receiver, based upon the Motorola IC MC3359, used in pocket FM radios. Instead of the Motorola IC MC3359 chip, any one of its equivalent integrated circuits may be used in the present invention as well, such as Calmos Systems IC CA404, Harris IC CA3215, Hitachi IC HA12412, Lucent Technologies IC W2005, Motorola IC MC13135/MC13136, MC3363, MC3367, New Japan Radio Company IC NJM2241, Panasonic IC AN6162, Phillips International IC TDA7088, Sanyo IC LA3410, SGS-Thomson IC TDA7361, Siemens IC PMB2430 or TBA120.

The 10.7 MHz output signal from the Colpitts oscillator of FIG. 4 enters a double balance mixer DBM 70 of FIG. 5 through a pin 18, where it is down-converted to a signal with frequency of 455 KHz, and passed through a 455 KHz bandpass filter 72, between pin 3 and pin 5. Detection circuitry for recovering audio signal is a quadrature demodulator (FM DEMOD) 74 with external phase delay formed by a 120 pF, 1.0 µH LC circuit 76. Demodulator output leaves through pin 10 and enters an externally located audio frequency counter, shown in FIG. 6. Squelch circuit section, from the conventional receiver, is used with the Motorola IC MC3359 board to prevent counting when there is no input from the Colpitts oscillator and only noise signals are present. Under these conditions the audio output of the FM demodulator is switched to ground 82 by an audio mute switch 80.

FIG. 6 is a schematic illustration of an audio frequency counter with a timer, according to the preferred embodiment of the present invention. The audio frequency counter 90 inputs audio signal obtained in the FM demodulator of FIG. 5 by demodulation of the crystal resonant frequency, output from the Colpitts oscillator of FIG. 4. It then calculates the total concentration of the gas encountered in the laser resonant beam path 16, based on the shift in output frequency from the Colpitts oscillator of FIG. 4. A change in the gas concentration can also be calculated and is proportional to the shift in output frequency from the Colpitts oscillator of FIG. 4. Therefore, the concentration of HF gas $n_{HF}$ can be calculated from equation (9), when the crystal frequency change is known. Since the gas sensor's sensitivity is directly proportional to the chosen resonant frequency $v_0$, equation (9) could be used for the calibration of the device.

Timer 92 provides time used in calculations performed in the audio frequency counter 90. Calculations may be performed in a microprocessor which may be embedded within the audio frequency counter 90. The frequency counter 90 can also measure the rate of change in concentration of the gas, if concentration values are repeatedly measured and recorded over the duration of the laser operation, and the difference between some concentration values are calculated at certain times. Averaging of the results may also be obtained to provide the average gas concentration in time, or, if several gas sensors 19 are placed at different locations in the laser resonator beam path 16 as shown in FIG. 1, to calculate the average gas concentration in the laser resonator beam path 16.

The gas sensor 19 of the present invention has numerous benefits. Its high crystal frequency makes it a highly sensitive device, exceeding the requirements for HF concentration measurements within a laser resonator beam path 16 by an order of magnitude. The device is inexpensive as it is made from readily available off-the-shelf components and uses well understood and tested electrical circuits. Since it is small and inexpensive, many units may be placed strategically throughout the laser resonator beam path 16. The gas sensor 19 is efficient and easily calibratible by observing and recording the frequency change during immersion in known concentrations of the gas. The gas sensor 19 of the present invention is useful in all industries that use HF or DF gas, either as an etchant, or as a product or byproduct in such industries, such as the semiconductor and oil-refining industries. It is equally applicable to other gaseous industrial crystal etchants.

While this invention has been described with reference to its presently preferred embodiment(s), its scope is only limited insofar as defined by the following set of claims and all equivalents thereof. It is quite clear that the above description has been given purely by way of a non-restrictive example. The digital values have been given purely to illustrate the description. Those skilled in the art will appreciate that various adaptations and modifications of the just-described preferred embodiments can be configured without departing from the scope and spirit of the invention. Therefore, it is to be understood that, within the scope of the appended claims, the invention may be practiced otherwise than as specifically described herein.

What is claimed is:

1. A device for determining concentration of a gas in a chamber, said gas having ability to act as a crystal etchant, said device comprising:
   a crystal having an initial mass, wherein said crystal is placed in a chamber and subjected to a crystal erosion process by the gas;
   determining means, coupled to said crystal, for determining the crystal resonant frequency, said crystal resonant frequency changeable during the crystal erosion process as a result of a decrease in the initial mass of said crystal occurring during the crystal erosion process; and
   calculating means, coupled to said resonant frequency determining means, for calculating a change in the crystal resonant frequency to determine the concentration of the gas.

2. The device according to claim 1 wherein the means for determining the crystal resonant frequency comprises:
   an oscillator, and
   a crystal resonant frequency detector for obtaining and demodulating the crystal resonant frequency from the oscillator and supplying the crystal resonant frequency to the calculating means.

3. The device according to claim 2 wherein:
   the crystal comprises an AT-cut quartz crystal,
   the oscillator comprises a Colpitts oscillator,
   the crystal resonant frequency detector comprises an FM demodulator, and
   the calculating means having means for calculating a change in the gas concentration, a rate of change in the gas concentration, and means for averaging the calculated gas concentration.

4. The device according to claim 3 wherein said gas is selected from the group consisting of hydrofluoric acid (HF) and deuterium fluoric acid (DF) gas.

5. The device according to claim 1 further comprising an electronic box for storing the means for determining the crystal resonant frequency and the crystal.

6. The device according to claim 5, wherein the electronic box further comprising:
   a crystal holder for holding the crystal, said crystal holder having:
      a plurality of electrodes,
      a mounting means for attaching the crystal to the electronic box and providing easy replacement of the crystal, and
      a protective cover with windows over the crystal.

7. The device according to claim 6 wherein:
   the means for determining the crystal resonant frequency comprises a Colpitts oscillator, and
   the crystal comprises an AT-cut quartz crystal, and wherein the electronic box further comprising:
   a battery supply, and
   a crystal resonant frequency detector for obtaining the crystal resonant frequency from the oscillator, demodulating and supplying the crystal resonant frequency to the calculating means.

8. The device according to claim 7 wherein said calculating means having:
   a timer,
   means for imputing crystal resonant frequency, and
   means for calculating the gas concentration, proportional to the change in the crystal resonant frequency.

9. The device according to claim 8 wherein said calculating means further having means for calculating a change in the gas concentration, proportional to the change in the crystal resonant frequency.

10. The device according to claim 9 wherein said calculating means further having means for calculating a rate of change in the gas concentration, proportional to the change in the crystal resonant frequency.

11. The device according to claim 10 wherein said calculating means further having means for averaging the calculated gas concentration.

12. The device according to claim 11 wherein said gas is selected from the group consisting of hydrofluoric acid (HF) and deuterium fluoric acid (DF) gas.

13. A method for determining concentration of a gas in a chamber, said gas having ability to act as a crystal etchant, said method comprising the steps of;
    subjecting a crystal having an initial mass to a crystal erosion process by the gas;
    determining the crystal resonant frequency, said crystal resonant frequency changeable during the crystal erosion process as a result of a decrease in the initial mass of said crystal occurring during the crystal erosion process; and
    calculating a change in the crystal resonant frequency to determine the concentration of the gas.

14. The method according to claim 13 wherein the crystal comprises an AT-cut quartz crystal, and the step of determining the crystal resonant frequency being performable in an oscillator.

15. The method according to claim 14 wherein said gas is selected from the group consisting of hydrofluoric acid (HF) and deuterium fluoric acid (DF) gas.

16. The method according to claim 14 wherein the step of determining the crystal resonant frequency is performable in an electronic box, said electronic box having a crystal holder for holding the crystal, said crystal holder having a plurality of electrodes, and a mounting means for attaching the crystal to the electronic box and providing easy replacement of the crystal.

17. The method according to claim 16 wherein the determining step further comprises the step of obtaining the crystal resonant frequency from the oscillator, demodulating and supplying the crystal resonant frequency to the calculating means.

18. The method according to claim 17 wherein said calculating step further comprises the step of:
    calculating the gas concentration, proportional to the change in the crystal resonant frequency.

19. The method according to claim 18 wherein said calculating step further comprises the step of:
    calculating a change in the gas concentration, proportional to the change in the crystal resonant frequency.

20. The method according to claim 19 wherein said calculating step further comprises the step of:
    calculating a rate of change in the gas concentration, proportional to the change in the crystal resonant frequency.

21. The method according to claim 20 wherein said calculating step further comprises the step of:
    averaging the calculated gas concentration.

22. The method according to claim 21 wherein said gas is selected from the group consisting of hydrofluoric acid (HF) and deuterium fluoric acid (DF) gas.

23. A device for determining concentration of a gas in a chamber, said gas having ability to act as a crystal etchant, said device comprising:
    a crystal comprising an AT-cut quartz crystal placed in the chamber and subjected to erosion by the gas;
    determining means, coupled to said crystal, for determining the crystal resonant frequency, said crystal resonant frequency changeable during the crystal erosion, the determining means comprising:
        an oscillator comprising a Colpitts oscillator; and
        a crystal resonant frequency detector for obtaining and demodulating the crystal resonant frequency from the oscillator and supplying the crystal resonant frequency to the calculating means, the crystal resonant frequency detector comprising an FM demodulator; and
    calculating means, coupled to said resonant frequency determining means, for calculating a change in the crystal resonant frequency to determine the concentration of the gas, the calculating means having means for calculating a change in the gas concentration, a rate of change in the gas concentration, and means for averaging the calculated gas concentration.

24. The device according to claim 23 wherein said gas is selected from the group consisting of hydrofluoric acid (HF) and deuterium fluoric acid (DF) gas.

25. A device for determining concentration of a gas in a chamber, said gas having ability to act as crystal etchant, said device comprising:
    a crystal comprising an AT-cut quartz crystal placed in the chamber and subjected to erosion by the gas;
    determining means, coupled to said crystal, for determining the crystal resonant frequency, said crystal resonant frequency changeable during the crystal erosion, the determining means comprising a Colpitts oscillator;
    calculating means, coupled to said resonant frequency determining means, for calculating a change in the crystal resonant frequency to determine the concentration of the gas; and
    an electronic box for storing the means for determining the crystal resonant frequency and the crystal, wherein the electronic box comprises;
        a crystal holder for holding the crystal, said crystal holder having:
            a plurality of electrodes;
            a mounting means for attaching the crystal to the electronic box and providing easy replacement of the crystal;
            a protective cover with windows over the crystal;
        a battery supply; and
        a crystal resonant frequency detector for obtaining the crystal resonant frequency from the oscillator, demodulating and supplying the crystal resonant frequency to the calculating means.

26. The device according to claim 25 wherein said calculating means having:
    a timer,
    means for imputing crystal resonant frequency, and
    means for calculating the gas concentration, proportional to the change in the crystal resonant frequency.

27. The device according to claim 26 wherein said calculating means further having means for calculating a change in the gas concentration, proportional to the change in the crystal resonant frequency.

28. The device according to claim 27 wherein said calculating means further having means for calculating a rate of change in the gas concentration, proportional to the change in the crystal resonant frequency.

29. The device according to claim 28 wherein said calculating means further having means for averaging the calculated gas concentration.

30. The device according to claim 29 wherein said gas is selected from the group consisting of hydrofluoric acid (HF) and deuterium fluoric acid (DF) gas.

31. A method for determining concentration of a gas in a chamber, said gas having ability to act as crystal etchant, said method comprising the steps of:
subjecting a crystal to erosion by the gas, wherein the crystal comprises an AT-cut quartz crystal;
determining the crystal resonant frequency, said crystal resonant frequency changeable during the crystal erosion, the step of determining the crystal resonant frequency being performable in a device selected from the group consisting of an oscillator, an electronic box, and combinations thereof, said electronic box having a crystal holder for holding the crystal, said crystal holder having a plurality of electrodes, and a mounting means for attaching the crystal to the electronic box and providing easy replacement of the crystal;
obtaining the crystal resonant frequency from the device selected from the group consisting of an oscillator, an electronic box, and combinations thereof, demodulating and supplying the crystal resonant frequency to a calculating means;
calculating a change in the crystal resonant frequency to determine the concentration of the gas;
calculating the gas concentration, proportional to the change in the crystal resonant frequency;
calculating a change in the gas concentration, proportional to the change in the crystal resonant frequency; and
calculating a rate of change in the gas concentration, proportional to the change in the crystal resonant frequency.

32. The method according to claim 31 further comprising the step of:
averaging the calculated gas concentration.

33. The method according to claim 31 wherein said gas is selected from the group consisting of hydrofluoric acid (HF) and deuterium fluoric acid (DF) gas.

* * * * *